United States Patent
Jang

(10) Patent No.: US 11,759,406 B2
(45) Date of Patent: Sep. 19, 2023

(54) MEDICAL CEMENT COMPOSITION

(71) Applicant: Maruchi Co., Ltd., Wonju-si (KR)

(72) Inventor: Sung-Wook Jang, Seoul (KR)

(73) Assignee: Maruchi Co., Ltd., Wonju-si (KR)

( * ) Notice: Subject to any disclaimer, the term of this patent is extended or adjusted under 35 U.S.C. 154(b) by 61 days.

(21) Appl. No.: 17/479,358

(22) Filed: Sep. 20, 2021

(65) Prior Publication Data

US 2022/0087907 A1    Mar. 24, 2022

(30) Foreign Application Priority Data

Sep. 21, 2020   (KR) .......................... 1020200121240

(51) Int. Cl.
| | |
|---|---|
| *A61K 6/871* | (2020.01) |
| *A61K 6/84* | (2020.01) |
| *A61K 6/60* | (2020.01) |

(52) U.S. Cl.
CPC ................ *A61K 6/871* (2020.01); *A61K 6/60* (2020.01); *A61K 6/84* (2020.01)

(58) Field of Classification Search
CPC ............. A61K 6/871; A61K 6/60; A61K 6/84
See application file for complete search history.

(56) References Cited

U.S. PATENT DOCUMENTS

| | | |
|---|---|---|
| 8,801,846 B2 | 8/2014 | Jang |
| 9,445,973 B2 | 9/2016 | Jang |
| 9,668,825 B2 | 6/2017 | Chow et al. |
| 2008/0085948 A1 | 4/2008 | Primus et al. |
| 2008/0210125 A1 | 9/2008 | Hermansson et al. |
| 2008/0302276 A1* | 12/2008 | Perez-Pena ............. C04B 28/04 106/690 |
| 2013/0025498 A1 | 1/2013 | Richard et al. |
| 2014/0322144 A1 | 10/2014 | Athanassiadis et al. |
| 2016/0318802 A1* | 11/2016 | Ferrari ................ C04B 22/0086 |
| 2016/0361237 A1 | 12/2016 | Jang et al. |
| 2017/0181931 A1 | 6/2017 | Jang et al. |
| 2019/0046418 A1 | 2/2019 | Rangabhatla et al. |
| 2019/0321267 A1 | 10/2019 | Jang |
| 2020/0138676 A1 | 5/2020 | Kim et al. |

FOREIGN PATENT DOCUMENTS

| | | | |
|---|---|---|---|
| JP | 2017506648 | 3/2017 | |
| JP | 2019535738 | 12/2019 | |
| KR | 20050071529 | 7/2005 | |
| KR | 20190046277 | 5/2019 | |
| WO | 2011124841 | 10/2011 | |
| WO | WO-2019093568 A1 * | 5/2019 | ........... A61K 6/0038 |

OTHER PUBLICATIONS

Extended Search Report from related European Application No. 2194910.2, dated Feb. 16, 2022, 11 pages.
Office Action from related Korea Patent Application No. 10-2020-0121240, dated Mar. 15, 2022, 4 pages.

* cited by examiner

*Primary Examiner* — Michael P Cohen
(74) *Attorney, Agent, or Firm* — Brooks, Cameron & Huebsch, PLLC

(57) ABSTRACT

The present disclosure relates to a medical cement composition containing calcium silicate in an amount of less than 20 wt % of a total weight of the composition, with a lithium salt being added thereto. The medical cement composition of the present disclosure has a low compressive strength of 12 MPa or less, after being hardened, for easy removal, excellent stability in storage, and high bioactivity.

5 Claims, 3 Drawing Sheets

MEDICAL CEMENT COMPOSITION

TECHNICAL FIELD

The present disclosure relates to a medical cement composition, and more particularly, to a medical cement composition for filling a space from which nerves, blood vessels, cellular tissues, hard tissues, and the like are removed.

BACKGROUND ART

In general, a medical filler composition, which is a material for filling a space from which nerves, blood vessels, cell tissues, hard tissues, and the like are removed for the purpose of treatment, has been applied in various fields.

The medical cement composition is essential in the dental field, especially in the field of endodontic treatment, in which nerves, blood vessels, and other tissues inside a tooth are removed, and the space is filled with and sealed by a material to maintain the function of the tooth.

As one type of medical cement composition, a mineral trioxide aggregate (MTA) is a material widely used for endodontic treatment, mainly for root perforation repair, pulpotomy, partial pulpotomy, pulp capping, root canal filling, root-end retrofilling, and the like. The MTA is advantageous in that sealing properties and biocompatibility are excellent, and is superior to calcium hydroxide, which is mainly applied to the treatment of vital tooth pulp, in terms of formation of tertiary dentin or infiltration of inflammatory cells.

In general, the MTA contains calcium silicate, calcium aluminate, and gypsum as main components, similar to Portland cement. When calcium silicate reacts with water in the presence of body fluid, saliva, other liquids, and the like, calcium silicate hydrate (C—S—H) and calcium hydroxide are produced.

The calcium silicate hydrate (C—S—H) has a variety of shapes, including coarse fibrous crystals and irregular and twisted nets. The calcium silicate hydrate (C—S—H) has a layer structure having a very high surface area and internal voids in a colloidal state, and occupies about 50 to 60% by volume of a hardened product of the MTA.

On the other hand, the calcium hydroxide has hexagonal plate-shaped crystals and occupies about 20 to 25% by volume of the hardened product of the MTA. An amount of calcium hydroxide is associated with the type of calcium silicate contained in MTA and the degree of hydration reaction.

The MTA has been spotlighted due to its high-level sealing properties and biocompatibility by showing revolutionary clinical results in many cases where treatment is difficult before the MTA is employed, but there is a concern that the MTA may weaken dentine because the MTA causes formation of calcium hydroxide.

As is the case with general calcium hydroxide formulations, if the root canal filling is performed using the MTA, the possibility of root fracture increases, and the dentine is physically eliminated in the process of endodontic treatment, thereby deteriorating the long-term prognosis of the endodontic treatment.

In order to solve this problem, U.S. Pat. No. 8,801,846 proposes a technique for neutralizing calcium hydroxide including a pozzolan material.

The MTA has better sealing properties than amalgam, IRM, and Super EBA, which have been conventionally used, but has problems in that it requires a long period of time for hardening, is inconvenient to operate, and causes discoloration. In addition, there is a problem in that the MTA is greatly affected by surrounding acidic environments in the process of hydrating the MTA, thereby weakening the physical properties and structure of the MTA. Even after the MTA is hardened, when the hardened product of the MTA is exposed to saliva or inflammatory products in an oral cavity, the saliva or inflammatory products react with calcium hydroxide therein, thereby rapidly weakening the structure and deteriorating the sealing properties.

This is because when the calcium hydroxide reacts with the saliva or the inflammatory exudate, calcium sulfate, sodium hydroxide, and magnesium hydroxide are produced, thereby increasing a volume, and accordingly causing an expansion pressure.

In fact, the molar volume of calcium hydroxide is 33.2 $cm^3$, while the molar volume of calcium sulfate is 74.2 $cm^3$. Therefore, when the calcium hydroxide is transformed to the calcium sulfate, the volume increases by about 2.2 times.

In addition, the calcium sulfate forms ettringite by reacting again with calcium aluminate hydrate, monosulfate, and tricalcium aluminate ($C_3A$). In this process, the volume also increases, thereby causing an expansion pressure, resulting in cracks in the hardened product. This is called alkali-aggregation reaction (AAR) in the art.

In order to solve this problem, studies have been conducted in the art so far, focusing on a method for neutralizing calcium hydroxide using a pozzolan reaction, in which silica and alumina active components react with calcium hydroxide in the presence of water to produce calcium silicate hydrate. Although the pozzolan reaction is advantageous in that durability can be improved and sealing properties can be better, the pozzolan reaction has little influence on bioactivity or biocompatibility.

In addition, the endodontic treatment is a treatment for disinfecting and sealing a complex endodontic system. Despite the developments in equipment and materials, it is known to be very difficult to completely disinfect and seal the endodontic system inside the tooth. In particular, the medical cement composition used for the endodontic treatment needs to be easily removed when re-treatment is required due to re-infection or the like even after being completely hardened after a procedure is finished.

In order to improve facilitation of re-treatment, U.S. Pat. No. 9,445,973 proposes a technique relating to a removable cement composition for root canal filling containing a zirconium oxide in an amount of 45% or more of the total amount of composition.

As another biggest disadvantage of the MTA, the MTA is not convenient to operate during the procedure. In order to overcome this disadvantage, U.S. Pat. No. 9,668,825 discloses a technique for providing MTA in a pre-mixed form.

In view of the technology development tendency so far, there is still a need for developing a medical cement composition that satisfies all of the following three conditions when used in a human body.

1) Excellent long-term stability achieved by inhibiting delayed expansion caused by calcium hydroxide
2) Low compressive strength enabling re-treatment
3) High bioactivity

RELATED ART DOCUMENT

Patent Document (Patent Document 1) U.S. Pat. No. 8,801,846
(Patent Document 2) U.S. Pat. No. 9,445,973
(Patent Document 3) U.S. Pat. No. 9,668,825

DISCLOSURE

Technical Problem

An object of the present disclosure is to provide a medical cement composition having a low compressive strength and a low calcium hydroxide production rate for excellent volume stability and high bioactivity.

In particular, the low compressive strength of the medical cement composition is a very useful property when re-treatment is necessary due to infection after treatment.

Technical Solution

The present disclosure provides a medical cement composition containing: calcium silicate in an amount of less than 20 wt % of a total weight of the composition; and a lithium salt.

Advantageous Effects

The medical cement composition of the present disclosure can be provided in a pre-mixed state. Therefore, it is easy to apply the medical cement composition in a process of treatment. Further, the medical cement composition of the present disclosure has a low compressive strength after being hardened. Therefore, it is easy to remove the medical cement composition when re-treatment is required. In addition, the medical cement composition of the present disclosure has excellent volume stability and high bioactivity.

BEST MODE

Figure 1A:
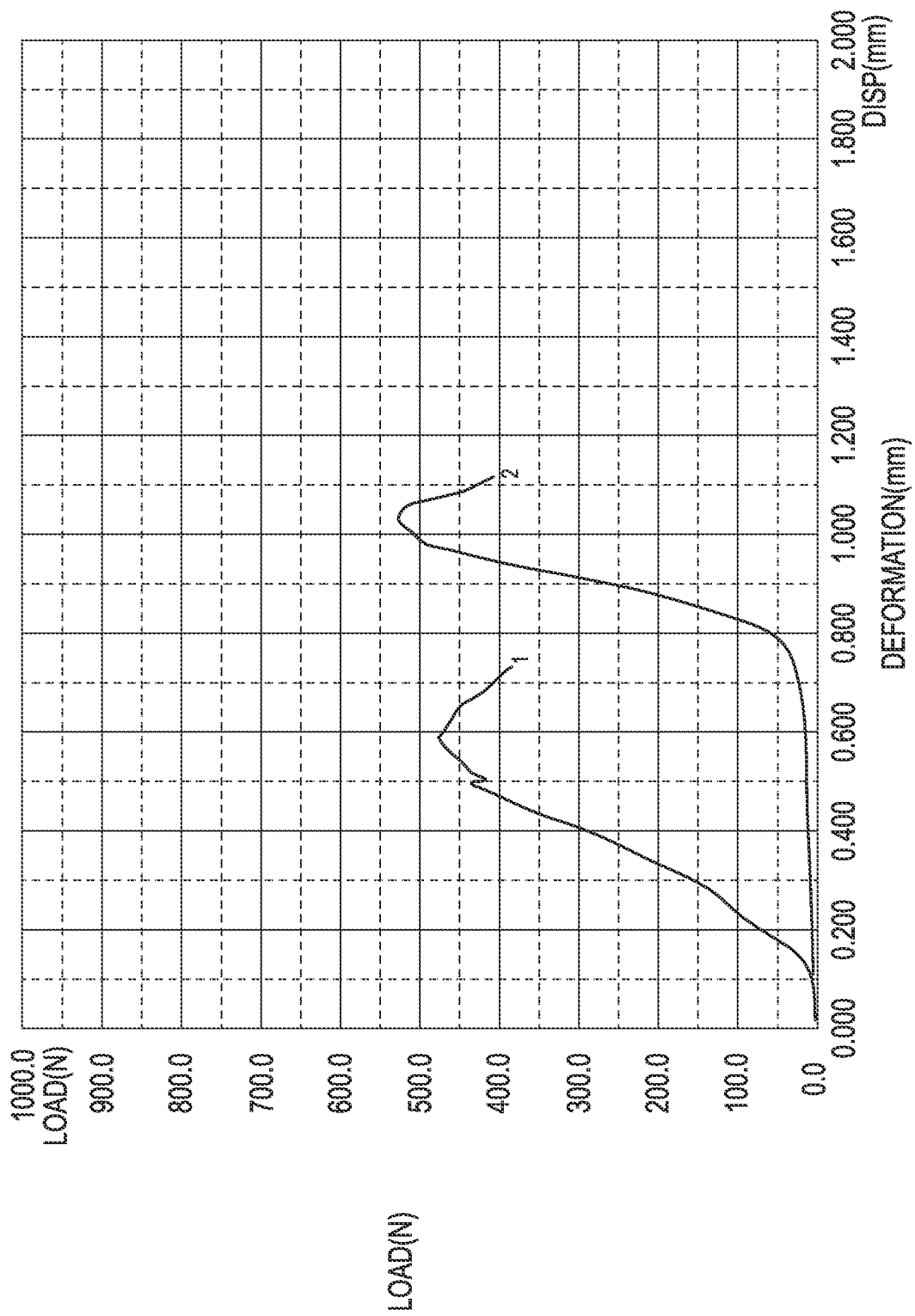
FIGS. 1A-1B show results of measuring compressive strengths of hardened products of medical cement compositions prepared according to Example 1 and Comparative Example 2.

Hereinafter, embodiments and examples of the present disclosure will be described in detail with reference to the accompanying drawings, so that the present disclosure can be easily implemented by those having ordinary knowledge in the art to which the present disclosure pertains. However, it is to be noted that the present disclosure is not limited to the embodiments and examples to be described below and may be embodied in many different forms. In drawings, parts irrelevant to the description are omitted to clearly illustrate the present disclosure.

Throughout the entire specification, when any part "comprises" or "includes" any element, it means that other elements are not precluded but may be further included, unless specifically otherwise stated.

Throughout the entire specification, the term "about" is used to mean "at" or "nearly at" a numerical value when manufacturing and material tolerances are inherent in the stated circumstances, and is used to prevent an accurate or absolute numerical value disclosed to facilitate understanding of the present disclosure from being illegally or unfairly used by unscrupulous infringers.

While endodontic treatment is intended for treating a tooth whose anatomical shape is complex and diverse and also requires a long period of time and complex equipment in the treatment process, its success rate is often unsatisfactory. If a first treatment is not successful, more nerve treatment or root-end surgery is often required before tooth extraction.

For such re-treatment, a filling material used in a previous procedure needs to be removed. At this time, if the root canal filling material is too hard, it is difficult to remove the filling material by a method commonly used by dentists, causing difficulty in re-treatment.

That is, it is necessary to appropriately decrease a compressive strength of the hardened filling material so that the hardened filling material can be removed when re-treatment is required.

The medical cement composition of the present disclosure may contain calcium silicate in an amount of less than 20 wt % of a total weight of the composition, preferably 5 wt % or more and less than 20 wt %. The calcium silicate may be water curable.

When the calcium silicate content is less than 5 wt % of the total weight of the cement composition, the cement composition greatly deteriorates not only in physical properties such as strength and sealing properties but also in bioactivity, and thus is not suitable for medical use.

When the calcium silicate content is 20 wt % or more of the total weight of the composition, the cement composition has a high compressive strength, making removal for re-treatment difficult.

In general, concerning the MTA composition, it has been known that the unique bioactivity of the MTA is expressed only when the calcium silicate content is at least 20 wt % or more of the total weight of the MTA.

It has been understood that the expression of the bioactivity is mainly affected by ionized calcium hydroxide, which is a product resulting from hydration reaction of the calcium silicate having hydration properties.

On the other hand, the calcium hydroxide weakens collagen fibers of a tooth root in the long term, leading to a problem that a fracture resistance of the tooth root is weakened, and causes delayed expansion due to alkali-aggregation reaction (AAR) after being hardened in vivo.

Thus, in order to reduce an absolute production amount of the calcium hydroxide, which is a product resulting from hydration reaction, there is a need for an additive capable of increasing bioactivity while decreasing an amount of the calcium silicate having hydration properties.

The medical cement composition of the present disclosure may further contain a lithium salt in an amount of 1.5 wt % or less based on 100 wt % of the calcium silicate contained in the amount of less than 20 wt % in the medical cement composition. Preferably, the lithium salt content may be 0.1 wt % or more and 1.5 wt % or less.

The lithium salt supplements the bioactivity of the medical cement, and at the same time, increases long-term volume stability of the medical cement hardened in the human body.

When the lithium salt is used in an amount of less than 0.1 wt %, the lithium salt has little effect in supplementing the bioactivity of the calcium silicate and inhibiting the alkali-aggregation reaction (AAR) of the calcium silicate. When the lithium salt is used in an amount of more than 1.5 wt %, the bioactivity of the medical cement composition rather deteriorates, resulting in an increase in production cost.

In addition, the lithium salt may be any one or more selected from the group consisting of lithium silicate, lithium nitride, lithium carbonate, and lithium hydroxide.

The calcium silicate of the present disclosure may be tricalcium silicate ($C_3S$). In particular, pure tricalcium silicate may be synthesized in advance for use in the preparation of the medical cement composition. Since the pure tricalcium silicate forms a filling product having a high compressive strength through its hydration reaction, if the pure tricalcium silicate is contained in an amount of 20% or more of the total weight of the medical cement composition, it may be difficult to remove the filling product after being hardened.

The medical cement composition of the present disclosure may preferably have a compressive strength of 3 MPa or more and 12 MPa or less to facilitate removal for re-treatment or the like. When the compressive strength is less than 3 MPa, the strength is so low that the hardened product of the medical cement composition is fragile even by a small impact after a procedure. On the other hand, when the compressive strength is more than 12 MPa, it is not easy to remove the hardened product of the medical cement composition for re-treatment.

In addition, the medical cement composition of the present disclosure may further contain, as a liquid component, any one or more selected from N-methyl-2-pyrrolidone (NMP), dimethyl sulfoxide (DMSO), and diethylene glycol monoethyl ether (DEGEE).

However, the liquid component is not particularly limited thereto, as long as it is a non-aqueous liquid with a low cytotoxicity while having a low viscosity in a polar solvent, being easily miscible with water, having penetration enhancing properties, and being safely usable in the human body.

In addition, the medical cement composition of the present disclosure preferably has radiopacity so that the progress of the procedure can be accurately checked through observation by radiographic examination. To this end, it is preferable that the medical cement composition of the present disclosure further contains radiopaque powder.

The radiopaque powder preferably includes any one or more selected from a ferroelectric, tungsten oxide, calcium tungstate, zirconium oxide, tantalum pentoxide, bismuth subnitrate, and barium sulfate.

Meanwhile, the radiopaque powder is preferably contained in an appropriate amount according to what the medical cement composition of the present disclosure is used for and the type of radiopaque powder.

More specifically, it is preferable that the radiopaque powder is contained in an amount of 40 to 60 wt % of the total weight of the medical cement composition.

Meanwhile, the medical cement composition of the present disclosure preferably contains, as a thickener for controlling rheological properties of the medical cement composition by imparting an appropriate viscosity thereto, any one or more selected from methylcellulose, hydroxyethylcellulose, hydroxypropylmethylcellulose, carboxymethylcellulose, polyvinyl alcohol, and polyvinyl pyrrolidone.

The liquid component and the thickener in the medical cement composition of the present disclosure are preferably contained in an amount of 15 to 35 wt % with respect to the total weight of the medical cement composition, in order to make the medical cement composition as a paste. This is because when they are contained in an amount of less than 15 wl %, it is difficult to make the medical cement composition as a paste for kneading, and when they are contained in an amount of more than 35 wt %, there is a problem in that the powder component is isolated due to the excessive liquid component.

In addition, the calcium silicate may have a size of 2 μm or less. When the size of the calcium silicate is more than 2 μm, aggregation occurs in a root canal, causing a problem that the progress of a GP cone is obstructed.

The medical cement composition of the present disclosure may be a dental cement composition. In particular, the medical cement composition of the present disclosure may be used for pulp capping, pulpotomy, retrofilling, perforation repair, root canal filling, and the like.

Meanwhile, the medical cement composition of the present disclosure is preferably formed in a paste type to be easily injected into a space requiring in-vivo repair and filling and to be easily stored. To this end, the medical cement composition of the present disclosure preferably contains a liquid material. That is, the medical cement composition of the present disclosure has a paste form by mixing and kneading the solid components with the liquid component.

In addition, the medical cement composition of the present disclosure may be provided in a pre-mixed form.

Hereinafter, the present disclosure will be described in more detail using a preparation example, a comparative example, and examples. All reagents used herein are those commercially available in general, and are used without being particularly purified, unless otherwise specified. Furthermore, the following preparation example, comparative example, and examples are only for illustrating the present disclosure and are not intended to limit the scope of the present disclosure.

Preparation Example 1

2 parts of hydroxypropyl methyl cellulose was added to a DMSO solution and completely dissolved therein. Thereafter, the DMSO solution and a powder component were kneaded in a ratio of 3:10 by weight, the powder component being obtained by mixing tricalcium silicate and zirconia ($ZrO_2$) in a ratio of 1:7, and a lithium salt additive was added thereto in a controlled amount to prepare a medical cement composition.

(The tricalcium silicate content of the medical cement composition prepared was 9.6 wt % of the total weight of the composition.)

Examples 1 to 7

Medical cement compositions were prepared according to the preparation method of Preparation Example 1, except that the lithium salt (lithium carbonate) contents of the medical cement compositions were 0.3, 0.5, 0.6, 0.7, 0.9, 1.2, and 1.5 wt %, respectively, as shown in Table 1 below, based on 100 wt % of the calcium silicate contained in the medical cement compositions.

TABLE 1

| Example | Lithium salt (lithium carbonate) content (wt %) |
|---|---|
| 1 | 0.3 |
| 2 | 0.5 |
| 3 | 0.6 |
| 4 | 0.7 |
| 5 | 0.9 |

TABLE 1-continued

| Example | Lithium salt (lithium carbonate) content (wt %) |
|---|---|
| 6 | 1.2 |
| 7 | 1.5 |

Comparative Example 1

A medical cement composition was prepared according to the preparation method of Preparation Example 1, except that the powder component was obtained by mixing tricalcium silicate and zirconia ($ZrO_2$) in a ratio of 1:3. That is, no lithium salt was included in Comparative Example 1.

(The tricalcium silicate content of the medical cement composition prepared was 20.03 wt % of the total weight of the composition.)

Test Example 1 (Compressive Strength)

Respective specimens of hardened products of the medical cement compositions of Example 1 and Comparative Example 1 were prepared, and compressive strengths thereof were measured (two specimens were prepared and measured in Example 1, and four specimens were prepared and measured in Comparative Example 1).

In order to measure a compressive strength, each of the samples prepared was implanted into a 10 mm*10 mm*10 mm square groove in an acrylic mold, and then the acrylic mold containing the sample was placed in a thermo-hygrostat under 36.5° C. and 100% conditions for hardening the sample.

Thereafter, the compressive strength of each of the specimens was measured using a universal testing machine (Model Name: Instron 5882). During the measurement, a maximum load was set to 5000 N, and a cross head speed was set to 0.85 mm/min.

Figure 1B:
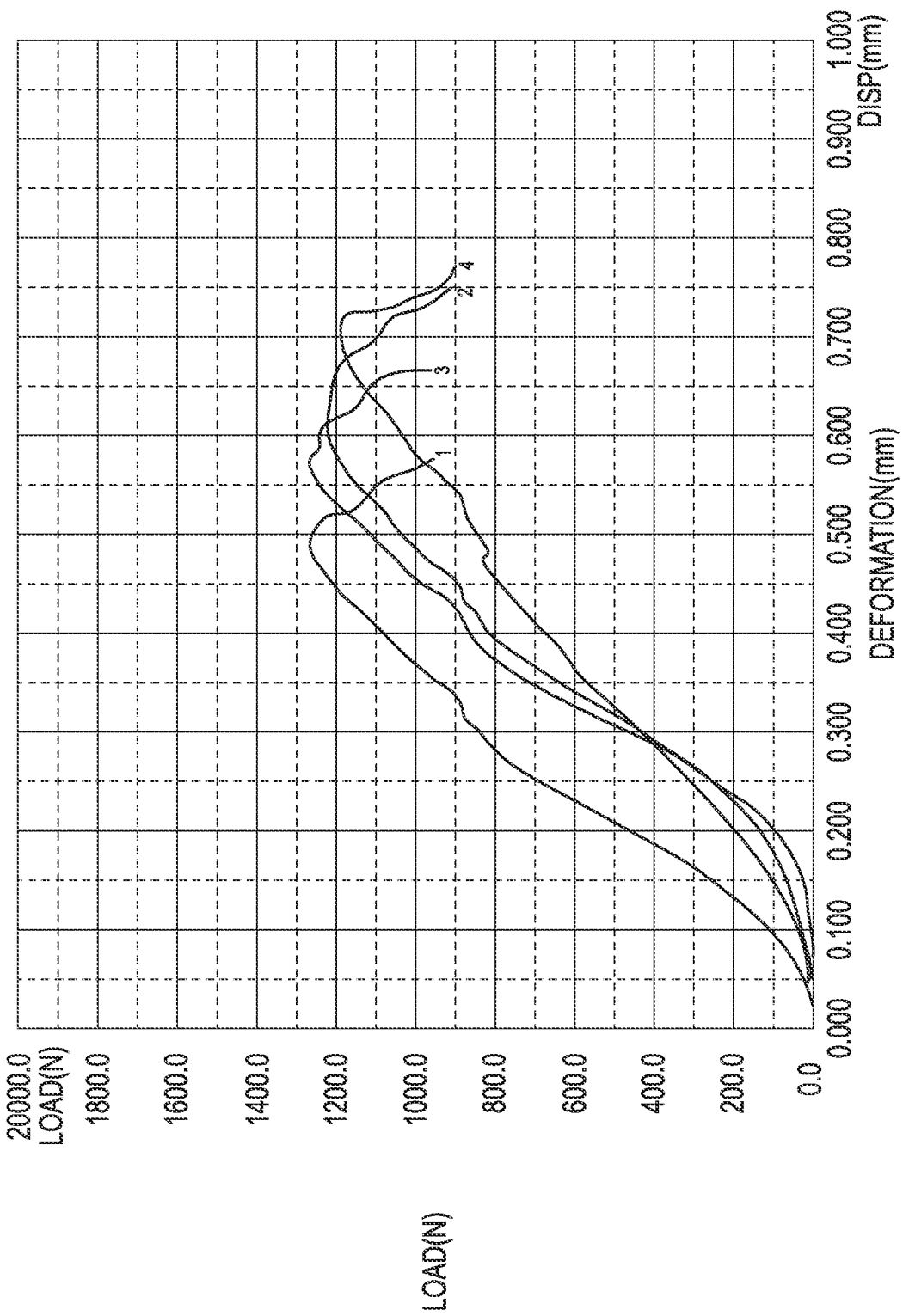

Measurement results are shown in FIGS. 1A-1B.

As shown in FIG. 1A, the hardened products of Example 1, which corresponds to a medical cement composition containing a lithium salt in an amount of 0.3 wt % with respect to the calcium silicate content, had an average compressive strength of about 5.034 MPa as measured.

In contrast, as shown in FIG. 1B, the hardened products of Comparative Example 1 had an average compressive strength of about 12.374 MPa as measured.

That is, the lower the calcium silicate (tricalcium silicate) content, the smaller the compressive strength. When the calcium silicate content was 20 wt % or more as in Comparative Example 1, the compressive strength was shown as exceeding 12 MPa, at which it might not be easy to remove the produced hardened product when re-treatment was required.

Therefore, it has been found that the calcium silicate content should be maintained to be less than 20 wt % of the total weight of the medical cement, in order to maintain the compressive strength of the produced hardened product at an appropriately low level, considering a case where re-treatment is required.

Test Example 2 (Cytotoxicity)

The hardened product of the medical cement composition was tested for cytotoxicity using an MTT analysis method. A specific test method will be described below.

After the hardened product of the medical cement composition was prepared as a specimen having a diameter of 10 mm and a thickness of 2 mm, the specimen was stored in an incubator at 37° C. under constant humidity for 3 to 7 days. Thereafter, the specimen was exposed to UV light overnight for sterilization, and then extracted at a concentration of 0.5 $cm^2$/ml in the 37° C. incubator for 3 days, and a supernatant of an extracted medium was isolated and stored. The MC3T3-E1 cell line to be used for the cytotoxicity test was cultured in an MEM-α medium with 10% FBS being added thereto. The MT3T3-E1 cell line was aliquoted into a 24-well plate at $1.5 \times 10_4$ cells per well and cultured for one day. At this time, samples were prepared in quadruplicate, and respective plates for days 1, 2, and 3 were prepared. Thereafter, the culture medium was removed from the cultured cell line, the extracted medium was aliquoted in an amount of 1 ml per well and cultured, and MTT assays were performed on days 1, 2, and 3. First, the cell culture medium was removed, and each sample was treated with an 0.05% MTT solution dissolved in PBS in an amount of 200 μm, and then cultured in the incubator at 37° C. for 2 hours. Thereafter, a DMSO solution was added in an amount of 200 μm to each sample. After 10 minutes, 200 μm of each sample is taken into a 96-well plate, and an optical density (OD) was measured to evaluate a cell survival rate. Here, the cell survival rate was determined using a mean and a standard deviation of measurement results between three test groups.

Figure 2:
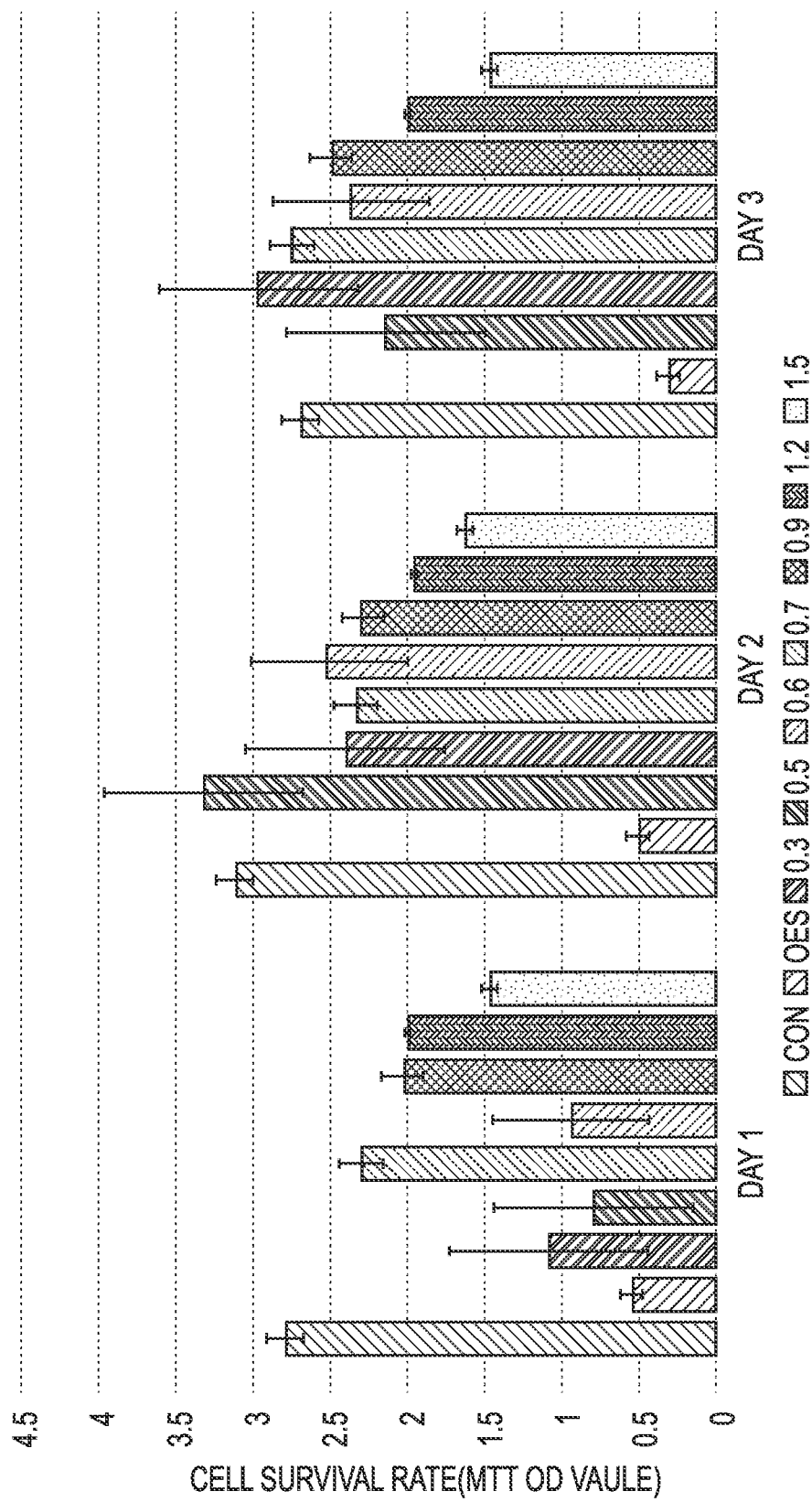
FIG. 2 shows results of testing hardened products of medical cement compositions prepared according to Preparation Example 1 and Examples 1 to 7 for cytotoxicity.

The results of testing the hardened products of the medical cement compositions for cytotoxicity through the MTT analysis method are shown in FIG. 2.

FIG. 2 shows cell survival rates for a control (CON) to which a hardened product of a medical cement composition is not applied, for a hardened product of a medical cement composition containing no lithium salt (OES, corresponding to Preparation Example 1), and for hardened products of medical cement compositions in Examples 1 to 7 (when the lithium salt contents are 0.3, 0.5, 0.6, 0.7, 0.9, 1.2, and 1.5 wt %, respectively, based on 100 wt % of the tricalcium silicate).

(The graph of FIG. 2 shows results of measuring cell survival rates in the hardened products of the medical cement compositions representing bar values for CON, OES, 0.3, 0.5, 0.6, 0.7, 0.9, 1.2, and 1.5 wt % as lithium salt contents, respectively, in order from the left to the right.)

First, the cell survival rate changes over time. However, it was confirmed that the cell survival rate in the hardened product of the medical cement composition containing no lithium salt was very lower than those in the hardened products of the medical cement compositions containing the lithium salt. This was more pronounced over time. It was also confirmed that the increase in bioactivity according to the increase in lithium salt content was maintained even after at least 3 days passed.

In addition, as a result of measurement over time, it was shown on day 3 that the cell activity was particularly high in the hardened products of the medical cement compositions in which the lithium salt is contained in the amount of 0.5 to 0.9 wt %, and the cell activity was somewhat low in the hardened products of the medical cement compositions in which the lithium salt is contained in the amount of 0.3 wt % and 0.9 to 1.5 wt %.

From the above-described test results, it was found that the cell activity in medical cement composition containing less than 20 wt % of calcium silicate could be improved by adding a lithium salt. In addition, it was confirmed that the cell activity could be optimized when the lithium salt is contained in the amount of 1.5 wt % or less in the medical cement composition.

That is, it was found that the cell activity in the hardened product of the medical cement composition of the present disclosure was very good.

The examples of the medical cement composition according to the present disclosure are merely preferred examples for those having ordinary knowledge in the art to which the present disclosure pertains to easily implement the present disclosure, and the present disclosure is not limited to the above-described examples and the accompanying drawings, and thus, the scope of the present disclosure is not limited thereto. Therefore, it is to be understood that the true technical protection scope of the present disclosure is defined by the technical spirit of the appended claims. In addition, it will be apparent to those skilled in the art that various substitutions, modifications, and changes may be made without departing from the technical spirit of the present disclosure, and the substitutions, modifications, and changes fall within the scope of the present disclosure.

The invention claimed is:

1. A medical cement composition, comprising:
    calcium silicate in an amount of 5 wt % or more and less than 20 wt % of a total weight of the composition; and
    a lithium salt in an amount of 0.3 wt % or more and 1.5 wt % or less based on 100 wt % of the calcium silicate
    wherein the medical cement composition has a compressive strength of 3 MPa or more and 12 MPa or less after being hardened.

2. The medical cement composition of claim 1, wherein the lithium salt is any one or more selected from the group consisting of lithium silicate, lithium nitride, lithium carbonate, and lithium hydroxide.

3. The medical cement composition of claim 1, wherein the calcium silicate is tricalcium silicate.

4. The medical cement composition of claim 1, further comprising any one or more selected from N-methyl-2-pyrrolidone (NMP), dimethyl sulfoxide (DMSO), and diethylene glycol monoethyl ether (DEGEE).

5. The medical cement composition of claim 1, wherein the medical cement composition is pre-mixed.

\* \* \* \* \*